(12) United States Patent
Delalic et al.

(10) Patent No.: US 7,101,343 B2
(45) Date of Patent: Sep. 5, 2006

(54) IMPLANTABLE TELEMETRIC MONITORING SYSTEM, APPARATUS, AND METHOD

(75) Inventors: Z. Joan Delalic, Bryn Mawr, PA (US); Michael R. Ruggieri, Sr., King of Prussia, PA (US); Michel A. Pontari, Lafayette Hill, PA (US); Bujjibabu Godavarthi, Philadelphia, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 323 days.

(21) Appl. No.: 10/702,265

(22) Filed: Nov. 5, 2003

(65) Prior Publication Data
US 2005/0096562 A1 May 5, 2005

(51) Int. Cl.
A61B 5/103 (2006.01)
(52) U.S. Cl. ..................................... 600/587
(58) Field of Classification Search ............... 600/29,
600/30, 31, 135, 561, 585, 587; 601/4, 151,
601/152, 153; 604/66, 67; 607/40, 41; 606/191,
606/192, 46, 47; 128/903, DIG. 25
See application file for complete search history.

(56) References Cited

U.S. PATENT DOCUMENTS

| | | | |
|---|---|---|---|
| 4,177,800 A | 12/1979 | Enger | |
| 4,519,401 A * | 5/1985 | Ko et al. | 600/561 |
| 4,703,756 A | 11/1987 | Gough et al. | |
| 5,205,294 A | 4/1993 | Flach et al. | |
| 5,446,246 A | 8/1995 | Desai et al. | |
| 5,562,713 A * | 10/1996 | Silvian | 607/32 |
| 6,033,366 A | 3/2000 | Brockway et al. | |
| 6,083,174 A | 7/2000 | Brehmeier-Flick et al. | |
| 6,206,835 B1 * | 3/2001 | Spillman et al. | 600/485 |
| 6,263,245 B1 * | 7/2001 | Snell | 607/60 |
| 6,296,615 B1 | 10/2001 | Brockway et al. | |
| 6,319,208 B1 * | 11/2001 | Abita et al. | 600/561 |
| 6,409,674 B1 | 6/2002 | Brockway et al. | |
| 6,507,759 B1 * | 1/2003 | Prutchi et al. | 607/60 |
| 6,658,300 B1 * | 12/2003 | Govari et al. | 607/60 |
| 6,897,788 B1 * | 5/2005 | Khair et al. | 340/870.16 |

OTHER PUBLICATIONS

W. Mokwa and U. Schnakenberg, On-Chip Microsystems for Medical Applications, Proc. Microsystem Symposium, 1998, Deift, Sep. 10-11, 1998, pp. 1-13.

Andrew Dehennis and Kensall D. Wise, A Passive-Telemetry-Based Pressure Sensing System, Digest of Solid-State Sensor and Actuator Workshop, Hilton Head, Jun. 2002.

Zoubir Hamici, Roland Itti and Jacques Champier, a high-efficiency power and data transmission system for biomedical implanted electronic devices, Meas. Sci. Technol. 7, 1996, pp. 192-201, Printed in the UK.

(Continued)

Primary Examiner—Max F. Hindenburg
Assistant Examiner—Vikram P. Sundararaman
(74) Attorney, Agent, or Firm—RatnerPrestia

(57) ABSTRACT

Systems, apparatus, and methods are disclosed for telemetrically monitoring parameters within a body of an animal such as a within a urinary bladder of a human. The system includes an implantable device configured for insertion within the body and an external device for use external to the body. The implantable device senses and stores one or more bodily parameters and transmits the stored bodily parameters for receipt by the external device responsive to receipt of a parameter transfer signal. The external device communicates with the implantable device, generates the parameter transfer signal, and receives the bodily parameters transmitted by the implantable device.

5 Claims, 7 Drawing Sheets

OTHER PUBLICATIONS

W. Stephen Woodward, Programmable Pressure Transducer, Electronic Design, May 15, 2000, pp. 125-126.

Kenneth W. Fernald et al., A Self-Tuning Digital Telemetry IC for Use in a Microprocessor-Based Implantable Instrument, IEEE Journal of Solid-State Circuits, vol. 27, No. 12, Dec. 1992, pp. 1826-1832.

K. Stangel et al., A Programmable Intraocular CMOS Pressure Sensor System Implant, IEEE Journal of Solid-State Circuits 36 (2001) 7, S. 1094-1100.

Qiuting Huang et al., A 0.5-mW Passive Telemetry IC for Biomedical Applications, IEEE Journal of Solid-State Circuits, vol. 33, No. 7, Jul. 1998, pp. 937-945.

Andrew Dehennis and Kensall D. Wise, A Double-Sided Single-Chip Wireless Pressure Sensor, Digest IEEE Conference on MicroElectroMechanical Systems, Las Vegas, Jan. 2002, pp. 252-255.

* cited by examiner $V_{in}$: input voltage  $V_r$: reference voltage
$V_{x(i)}$: intermediate voltage  $b_i$: output bits
$V_{th}$: threshold voltage  n: number of bits

IMPLANTABLE TELEMETRIC MONITORING SYSTEM, APPARATUS, AND METHOD

FIELD OF THE INVENTION

The present invention relates to the field of medicine and, more particularly, to telemetric monitoring systems, apparatus, and methods for monitoring bodily parameters obtained from an implantable device inserted within the body of an animal, for example, measuring and monitoring pressure within a urinary bladder of a human.

BACKGROUND OF THE INVENTION

The monitoring of bodily parameters within a body, such as fluid pressure in a urinary bladder of a human, is an important tool for medical research and clinical diagnosis. For example, fluid pressure within a urinary bladder is useful in diagnosing the cause of urinary incontinence. Urinary bladder over-activity or urge incontinence is generally due to a urinary bladder that contracts too much or at inappropriate times and, thus, is often associated with elevated fluid pressure levels within the urinary bladder. Stress incontinence, on the other hand, is generally due to a sphincter that does not stay sufficiently closed or opens at inappropriate times and, thus, is often associated with normal fluid pressure levels within the urinary bladder. In order to design an effective treatment strategy, it is critical to evaluate the cause of the incontinence so that therapy can be appropriately directed, for example, towards the urinary bladder or the sphincter. Therefore, systems, apparatus, and methods for measuring bodily parameters within a body of a human are useful.

Typically, to measure fluid pressure within a body, an implantable device is inserted into the body for the purpose of measuring pressure therein. The implantable device obtains fluid pressure measurements and transfers the pressure measurements to an external device for recording and/or display, for example, on a monitor or on paper. In existing devices, such as described in U.S. Pat. No. 6,319,208 to Abita et. al. entitled TELEMETRIC IN VIVO BLADDER URINE MONITOR SYSTEM and U.S. Pat. No. 6,409,674 to Brockway et al. entitled IMPLANTABLE SENSOR WITH WIRELESS COMMUNICATION, the implantable device must be within communication distance of the external device in order to capture pressure readings. Accordingly, the mobility of a patient in which the implantable device is inserted is encumbered by the mobility of the external device.

Accordingly, methods, systems, and apparatus are needed to measure bodily parameters such as fluid pressure within a body of an animal that are not subject to the above limitation. The present invention fulfills this need among others.

SUMMARY OF THE INVENTION

The present invention includes a telemetric monitoring system for monitoring parameters within a body of an animal such as fluid pressure within a urinary bladder of a human. The system includes an implantable device configured for insertion within the body and an external device for use external to the body. The implantable device senses and stores one or more bodily parameters and transmits the stored bodily parameters for receipt by the external device responsive to receipt of a parameter transfer signal. The external device communicates with the implantable device, generates the parameter transfer signal, and receives the bodily parameters transmitted by the implantable device.

Another aspect of the present invention is a telemetric monitoring method for monitoring parameters within a body of an animal. The method includes sensing and storing one or more bodily parameters within a body; generating a parameter transfer signal external to the body; receiving the parameter transfer signal within the body; responsive to receipt of the parameter transfer signal, transmitting the bodily parameters from within the body for receipt by a device (receiver) external to the body, and receiving external to the body the bodily parameters transmitted from within the body.

Another method includes sensing a bodily parameter, storing within the body readings corresponding to the sensed bodily parameter, receiving a parameter transfer signal within the body from a source external to the body, and transmitting the stored sensed bodily parameter reading from within the body for receipt external to the body responsive to the received parameter transfer signal.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Figure 1:
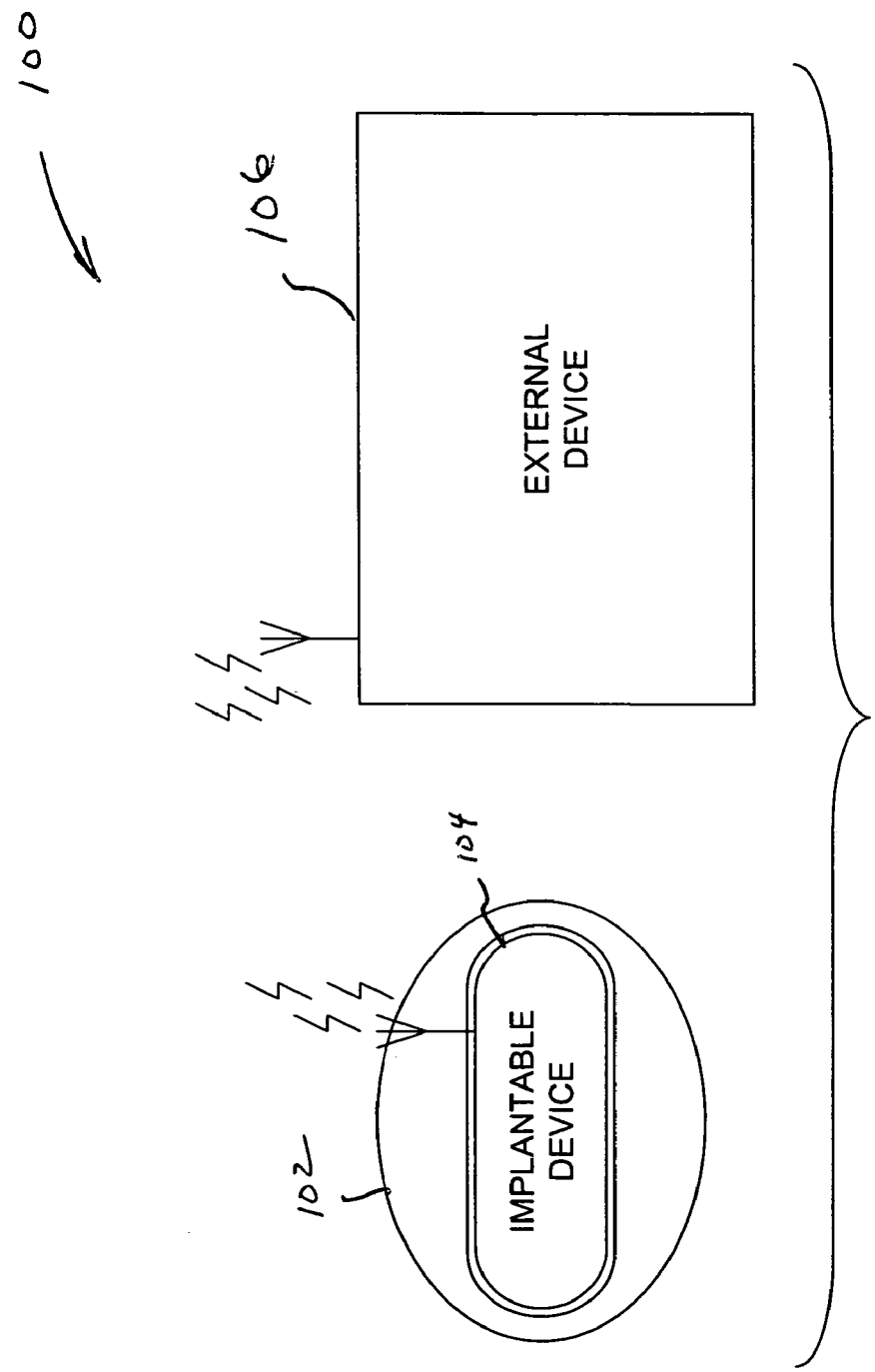
FIG. 1 is a block diagram of an exemplary telemetric monitoring system in accordance with the present invention.

FIG. 1 depicts an exemplary telemetric monitoring system 100 for monitoring bodily parameters such as pressure within a body 102 of an animal. The telemetric monitoring system 100 includes an implantable device 104 for insertion within the body 102 to monitor one or more bodily parameters therein and an external device 106 configured for communication with the implantable device 104.

In the detailed description below, the body 102 is a body cavity within an animal, such as a urinary bladder within a human, and the bodily parameter is fluid pressure. The telemetric monitoring system 100 described below may, however, be used to measure other bodily parameters including, by way of non-limiting example, non-fluid pressure, salinity, protein level, acidity, etc., and may be used within other body cavities including, by way of non-limiting example, the uterus, stomach, and bowel. In addition, the telemetric monitoring system 100 may be used in other animals including, by way of non-limiting example, mammals.

Figure 2:
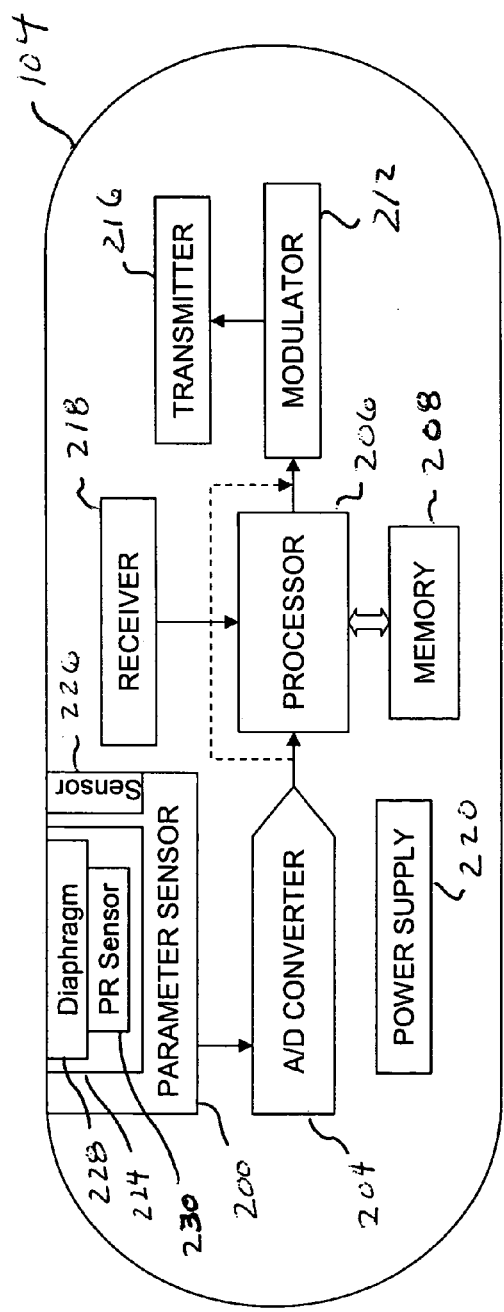
FIG. 2 is a block diagram of an exemplary implantable device in accordance with the present invention.

FIG. 2 depicts a detailed view of the implantable device 104. In an exemplary embodiment, a parameter sensor 200 is configured to sense a single bodily parameter within a body cavity 102, such as fluid pressure within a urinary bladder. In an alternative exemplary embodiment, the parameter sensor 200 includes more than one sensor for sensing multiple bodily parameters.

In the illustrated embodiment, the parameter sensor 200 includes a pressure sensor 224 and, optionally, one or more other sensors (represented by sensor 226). The illustrated pressure sensor 224 includes a diaphragm 228 that is responsive to pressure fluctuations and a piezoresistive (PR) sensor 230 coupled to the diaphragm 228 for sensing the pressure fluctuations. The piezoresistive sensor 230 generates a bodily parameter output signal at an output port. Changes in pressure cause displacements of the diaphragm 228 that, in turn, stress the piezoresistive sensor 230 to alter the electrical output characteristics of the bodily parameter output signal generated by the piezoresistive sensor 230. In alternative exemplary embodiments, other types of sensors may be used to sense pressure including, by way of non-limiting example, piezo-junction devices and capacitive pressure transducers.

The exemplary piezoresistive sensor is a Wheatstone bridge including silicon piezoresistive strain sensors located radially and tangentially on a diaphragm. These sensors are either epoxy bonded to a thin metal diaphragm or are formed as an integral part of a silicon diaphragm by a diffusion or an ion implantation process. In use, two of the opposing sensors increase in resistance and the other two decrease in resistance as the diaphragm is deflected. For radial and tangential sensors of the same value of resistance "R," the change in output voltage $\Delta Vo$ is approximately $\Delta Vo = Vs$ or $\Delta R/R$, where Vs is the transducer supply voltage and $\Delta R$ is the change in resistance caused by applied stress due to pressure. The change in output voltage with pressure $\Delta Vo/\Delta q$ (where q is applied pressure) varies depending upon the diaphragm materials and dimensions. Exemplary values for $\Delta Vo/\Delta q$ are 3 to 20 $\mu V/V/mmHg$ for a suitable piezoresistive pressure transducer.

An analog-to-digital (A/D) converter 204 digitizes an analog voltage level sample of the bodily parameter signal for processing by a processor 206. An exemplary A/D converter is a multi-stage A/D converter that uses a known redundant signed digit (RSD) algorithm.

Figure 4A:
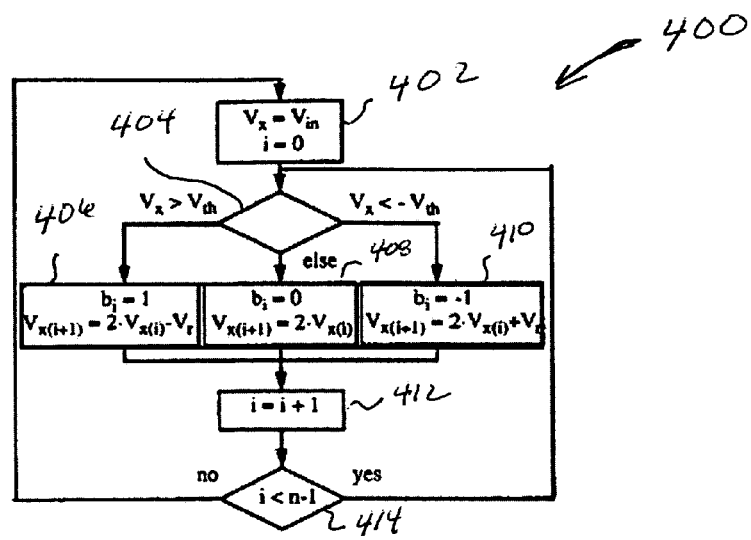
FIG. 4A is a flow chart of an exemplary algorithm for designing an A/D converter for use within the implantable device of FIG. 2.

FIG. 4A depicts a flow chart 400 of a suitable RSD A/D converter algorithm. At block 402, an intermediate voltage, Vx(i), for a first digital bit, i=0, is set equal to an input voltage, Vin. At block 404, a decision is performed regarding the voltage level of Vx(i) of the current bit. If Vx(i) is greater than a threshold value, Vth, processing proceeds at block 406 where bi is set to one (1) and Vx(i+1) is set equal to two (2) times Vx(i) minus (−) a reference voltage Vr. If Vx is equal to Vth, processing proceeds at block 408 where bi is set equal to zero (0) and Vx(i+1) is set equal to two (2) times Vx(i). If Vx is less than negative Vth (−Vth), processing proceeds at block 410 where bi is set equal to −1 and Vx(i+1) is set equal to two (2) times Vx(i) plus (+) a reference voltage Vr.

At block 412, the digital bit number is incremented by one and, at block 414, a decision is performed to determine if all bits have been determined. If all bits have not been determined (i<n−1), processing proceeds at block 404 to determine the value for the next digital bit. If all bits have been determined (i=n−1), processing proceeds at block 402 with the digitization of another analog voltage level sample.

Figure 4B:
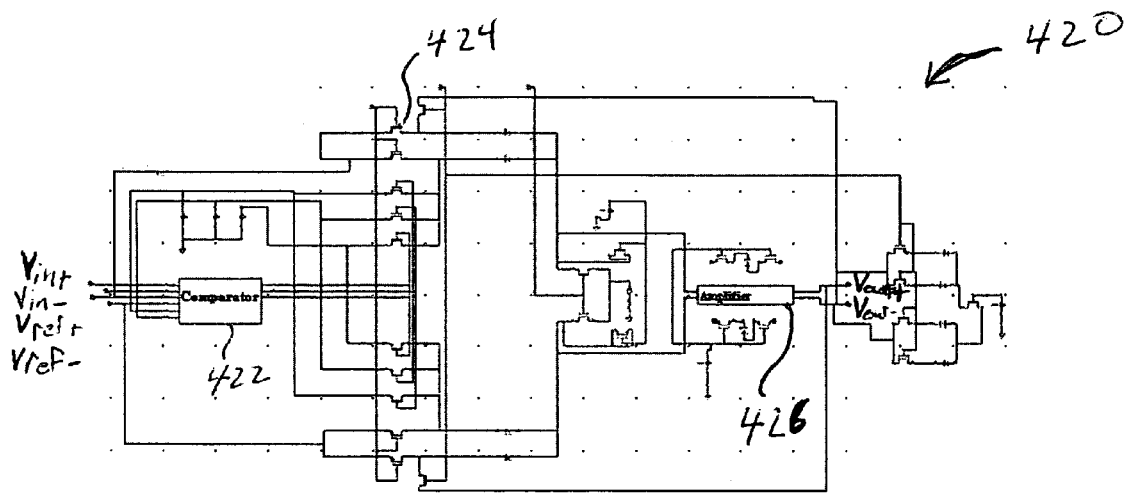
FIG. 4B is a circuit diagram of an exemplary single stage of a multi-stage A/D converter for use within the implantable device of FIG. 2.

FIG. 4B depicts a single stage 420 of an exemplary multi-stage A/D converter, with the number of stages in the A/D converter equal to the number of desired bits for each analog sample. For example, if an eight bit digital value is desired, eight of the signal stages depicted in FIG. 4B would be used. Bodily parameter signals from the parameter sensor 200 are applied to a comparator 422. The comparator 422 compares the bodily parameter signals to reference signals. For example, the comparator 422 may compare a differential input voltage value (Vin+, Vin−) representing fluid pressure to a differential reference voltage (Vref+, Vref−). The output of the comparator 422 and feedback signals based on the output values of the A/D converter are then used to actuate a plurality of switches (represented by NMOS transistor 424).

The resultant signals out of the comparator based on the plurality of switches is then amplified by the amplifier 426 to create an amplified differential output voltage (Vout+, Vout−). In an exemplary embodiment, the amplifier is a telescopic operational differential amplifier with folded common mode feedback. The amplified differential output voltage is fed to the input of the comparator of the next stage. The final output of the A/D converter is passed to the processor 206 for processing and/or the modulator 212 for modulation and transmission. In the illustrated stage 420 of the exemplary A/D converter, signals are processed differentially to reduce noise. In an exemplary embodiment, the A/D converter is fabricated using approximately 1 micron or smaller fabrication technology so that the A/D converter can be positioned within an implantable device 104 (FIG. 4) configured for insertion into a urinary bladder of a human/animal via a urethra. Suitable fabrication technologies, comparators, and amplifiers will be understood by those of skill in the art from the description herein.

Referring back to FIG. 2, the processor 206 is configured for use with a memory 208 and stores the bodily parameter information in the memory 208. In an exemplary embodiment, stored information within the memory 208 can be retrieved by the processor 206 or directly from the memory 208 when the implantable device is removed from the body 102. In an alternative exemplary embodiment, the stored information is retrieved by the processor 206 for transmission from within the body to the external device 106 (FIG. 1) while the implantable device 104 is still within the body 102, which is described in further detail below. In an alternative exemplary embodiment, the bodily parameters received from the A/D converter 204 are sent by the processor for essentially immediate transmission without first being stored in the memory 208. Suitable processors and memories for use in the present invention will be understood by those of skill in the art.

A modulator 212 modulates bodily parameter signals received from the processor 206 for transmission by the implantable device 104. The modulated bodily parameter signal is passed to a transmitter 216 for transmission from the implantable device 104 to the external device 106. Suitable modulators and transmitters will be understood by those of skill in the art.

A receiver 218 is configured to receive transmissions including instructions from the external device 106 and pass the instructions to the processor 206. The processor 206 is configured to receive and process the instructions from the receiver 218. In an exemplary embodiment, instructions received through the receiver 218 are used to configure the implantable device 104, which is described in further detail below. A power supply 220 supplies power to the various components within the implantable device 104. Connection lines between the power supply 220 and the individual components are omitted for clarity within the figure. Suitable receivers and power supplies will be understood by those of skill in the art.

In an exemplary embodiment, the implantable device 104 may be turned on and off remotely, for example, by the external device 106 (FIG. 1). When the implantable device is on, it records sensed bodily parameters sensed by the implantable device. When the implantable device is off, the implantable device does not record the sensed bodily parameters, thereby conserving power. The implantable device may be turned on and off via transmitted instructions received from the external device. In an alternative exemplary embodiment, the implantable device may be turned on and off responsive to configuration instructions stored in the implantable device either prior to insertion into the body or remotely by the external device prior to or after insertion into the body.

The implantable device is contained within a housing 222. In an exemplary embodiment, the housing 222, and component contained therein, are sized for insertion into a urinary bladder via the urethra, for example, the housing 222 measures less than 10 millimeters in diameter along at least one axis. In addition, the housing 222 is formed from a material suitable for use within the urinary bladder and is sufficiently buoyant to float within the urinary bladder such that it will not obstruct the urethra or be swept out of the urinary bladder during urination. A suitable housing 222 for use with the present invention will be understood by those of skill in the art.

Figure 3:
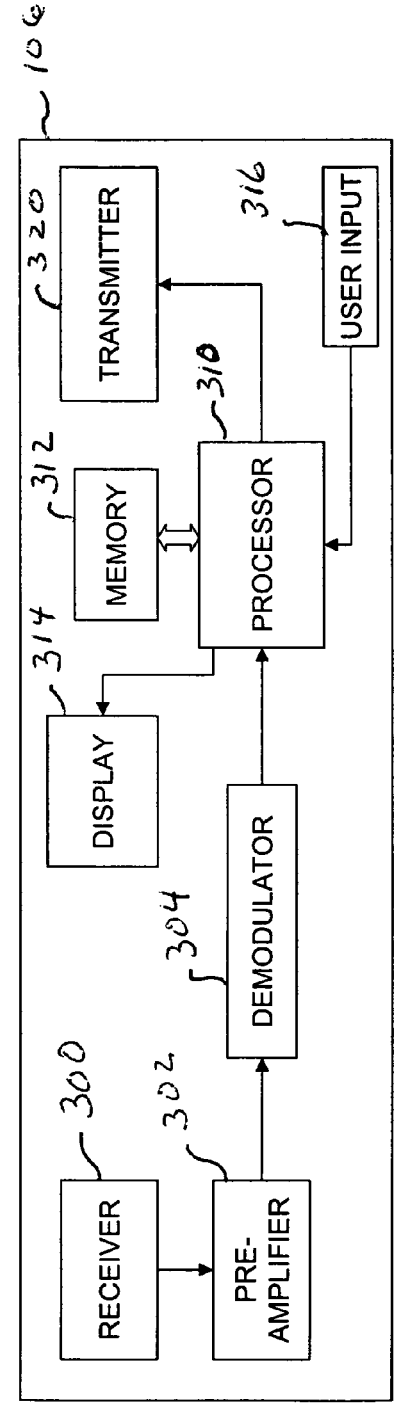
FIG. 3 is a block diagram of an exemplary external device in accordance with the present invention.

FIG. 3 depicts details of an exemplary external device 106. A receiver 300 is configured for communication with the implantable device 104. In an exemplary embodiment, signals received from the implantable device 104 at receiver 300 are modulated signals. A preamplifier 302 amplifies the modulated signals to a level suitable for use with a demodulator 304. The demodulator 304 demodulates the modulated signal to obtain the bodily parameter signal sensed by the implantable device 104 (FIG. 2). The demodulated bodily parameter signal is then processed by a processor 310. The processor 310 is configured for use with a memory 312. Suitable receivers, preamplifiers, demodulators, processors, and memories will be understood by those of skill in the art.

The processor 310 processes the bodily parameter information stored in the memory 312 and/or received directly from the receiver 300 for display on a display 314, such as a monitor and/or printer. In addition, the processor 310 generates instructions for configuring the implantable device 104 (FIG. 2). In an exemplary embodiment, the processor 310 generates a parameter transfer signal for instructing the implantable device to transmit stored bodily parameter signals. In addition, the processor may generate configuration instructions for the implantable device, such as instructions to turn the implantable device on and off.

A user input 316 receives information from an external source and passes the information to the processor 310. In an exemplary embodiment, the user input 316 generates a transfer request signal and the parameter transfer signal for instructing the implantable device to transmit stored bodily parameter signals is generated by the processor 310 in response to the transfer request signal. In an alternative embodiment, the parameter transfer signal is generated internally by the processor 310, for example, based on program instructions stored within the external device 106. The user input 316 may be a conventional input device such as a switch, keyboard, and/or a keypad. Information generated by the processor 310 for transmission from the external device 106 to the implantable device 104 is transmitted by a transmitter 320, which is configured for communication with the implantable device 104. A suitable transmitter for use with the present invention will be understood by those of skill in the art.

Figure 5:
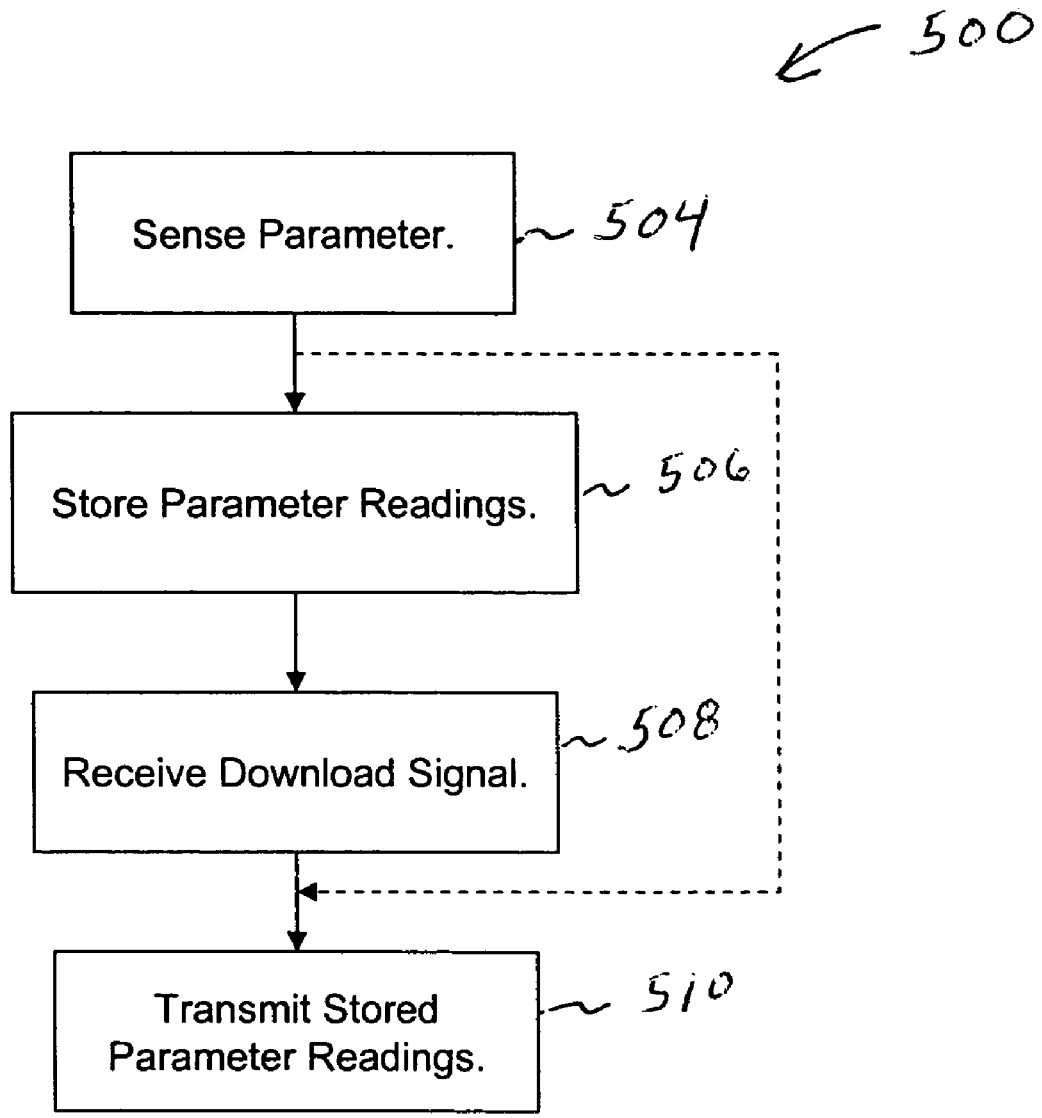
FIG. 5 is a flow chart of exemplary processing steps performed by the implantable device of FIG. 2 in accordance with the present invention.

FIG. 5 depicts a flow chart 500 of exemplary processing steps performed by an implantable device 104 (FIG. 2). Processing begins at block 504 with the sensing of one or more bodily parameters by the implantable device. At block 506, the parameter(s) sensed at block 504 are stored in the implantable device, for example, in a memory. At block 508, a parameter transfer signal is received at the implantable device, for example, from the external device 106 (FIG. 3). At block 510, the implantable device 104 retrieves the stored parameter readings and transmits the stored parameter reading stored at block 506 responsive to the parameter transfer signal received at block 508. In alternative exemplary processing steps, bodily parameters sensed at block 504 are substantially concurrently transmitted at block 510 without, or in addition to, performing the steps of blocks 506 and 508.

Figure 6:
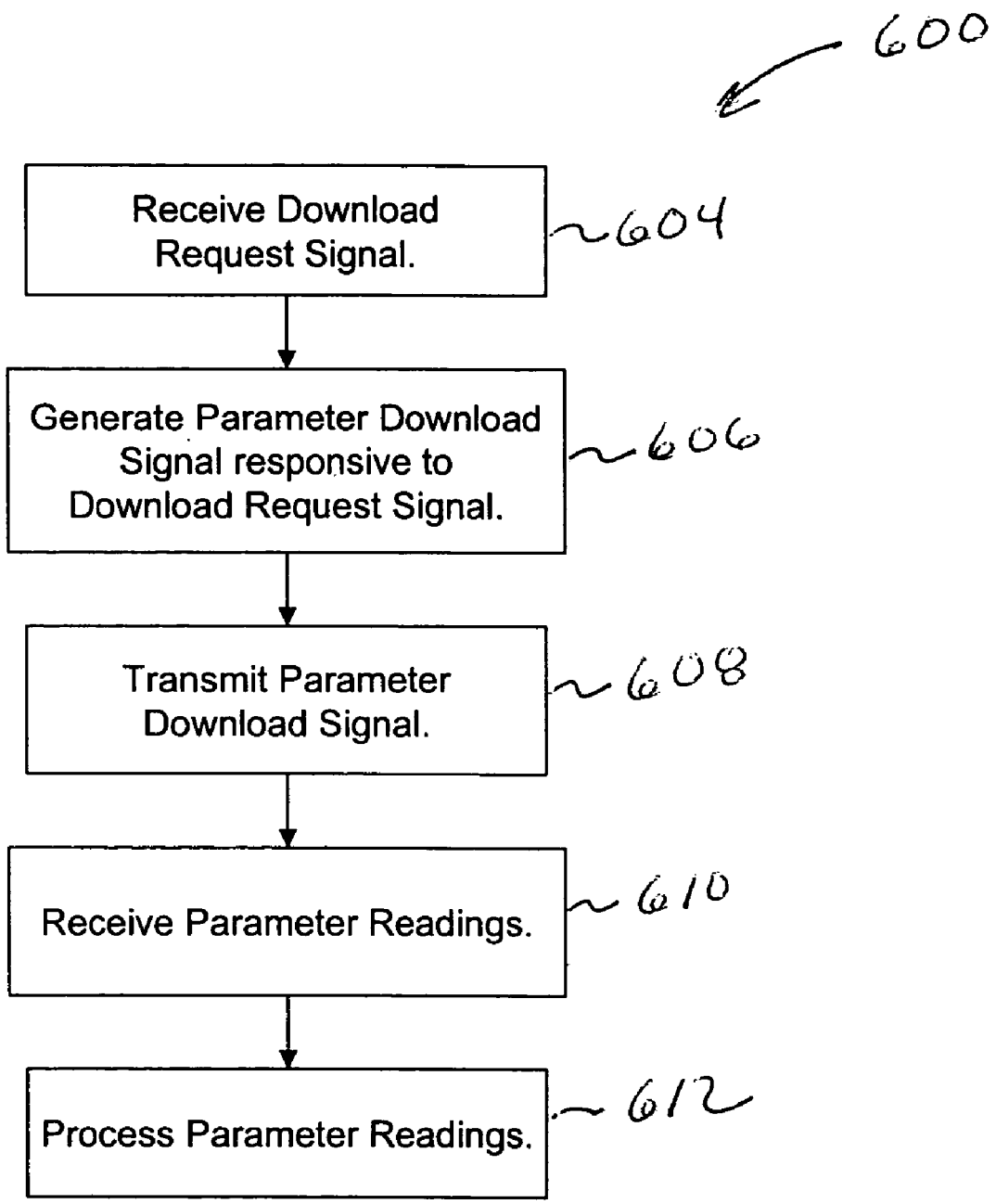
FIG. 6 is a flow chart of exemplary processing steps performed by the external device of FIG. 3 in accordance with the present invention.

FIG. 6 depicts a flow chart 600 of exemplary steps performed by an external device 106 (FIG. 3). Processing begins at block 604 with the receipt of a transfer request signal. In an exemplary embodiment, the transfer request signal is generated responsive to an external source such as a user via an input device. In an alternative embodiment, the transfer request signal is generated internally, for example, in response to predefined program instructions performed by a processor.

At block 606, a parameter transfer signal is generated in response to the transfer request signal. At block 608, the parameter transfer signal is transmitted by the external device for receipt by an implantable device 104 (FIG. 2), which transmits stored bodily parameters responsive to receipt of the parameter transfer signal.

At block 610, parameter readings are received at the external device from the implantable device. At block 612, the external device processes the stored bodily parameters received from the internal device, for example, for storage and/or display.

Figure 7:
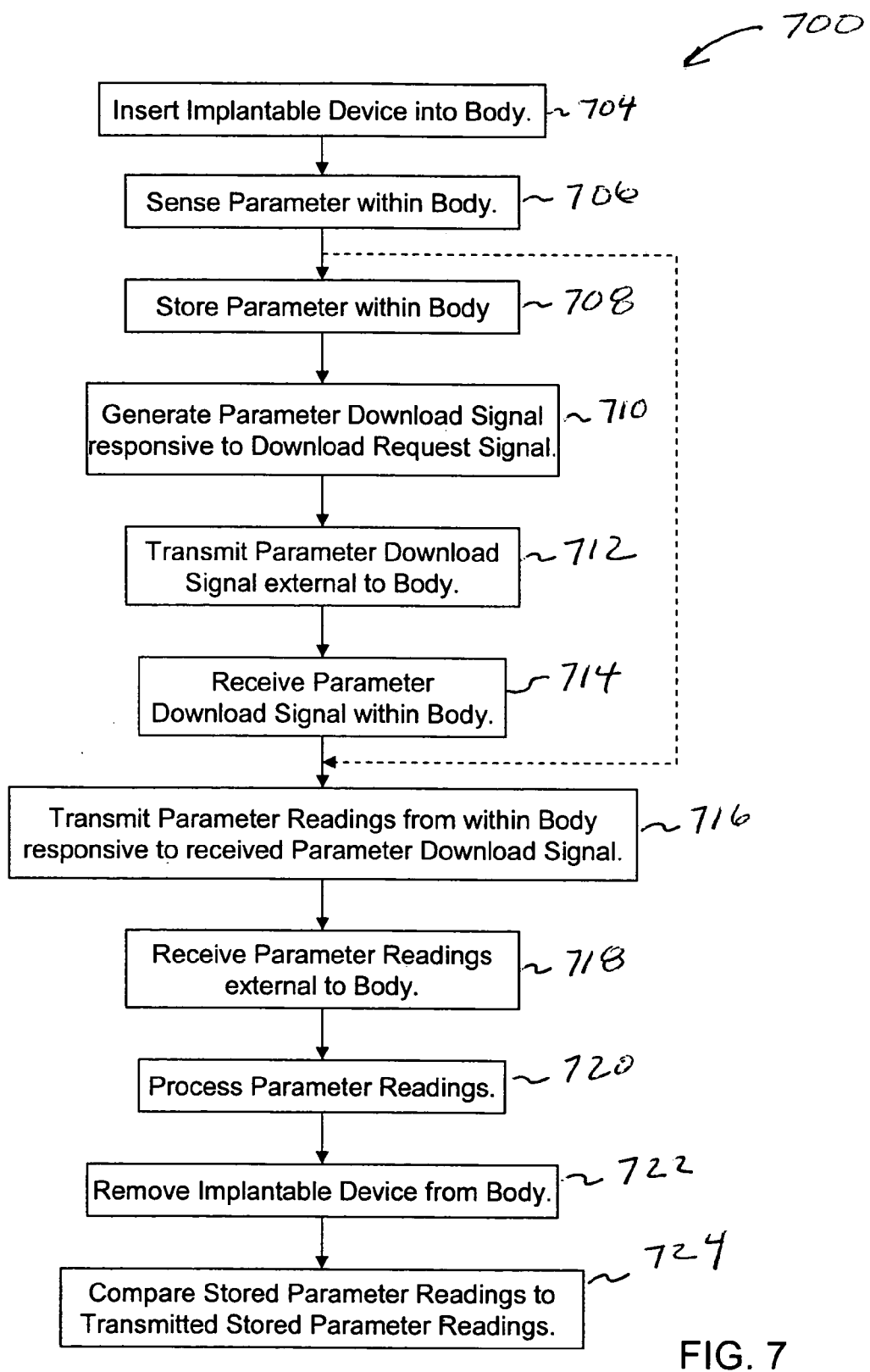
FIG. 7 is a flow chart of exemplary steps performed by the exemplary telemetric monitoring system of FIG. 1 in accordance with the present invention.

FIG. 7 depicts a flow chart 700 of exemplary steps for obtaining bodily parameters from within a body, such as fluid pressure within a urinary bladder. Processing begins at block 704 with the insertion of an implantable device 104 (FIG. 2) into the body. In an exemplary embodiment, the implantable device may be inserted and removed from the urinary bladder via the urethra of the animal using a known catheter like device (not shown).

At block 706, the implantable device senses one or more bodily parameters within the body. At block 708, the sensed bodily parameters are stored in the implantable device within the body, such as within a memory.

At block 710, a parameter transfer signal is generated at an external device 106 (FIG. 3) responsive to a transfer request signal, such as a signal generated by a user input of the external device. At block 712, the parameter transfer signal is transmitted by the external device external to the body for receipt by the implantable device internal to the body.

At block 714, the parameter transfer signal is received at the implantable device within the body. At block 716, the implantable device transmits the stored parameter readings from within the body responsive to the parameter transfer signal received at block 714 for receipt by the external device external to the body. In alternative exemplary processing steps, bodily parameters sensed at block 504 are substantially concurrently transmitted at block 510 without, or in addition to, performing the steps of blocks 506 and 508.

Because the implantable device is capable of storing parameter readings and, then, transmitting those parameter reading responsive to a parameter transfer signal, the implantable device is able to acquire readings for later transmission even when the implantable device is not within communication distance of the external device. Thus, the mobility of the patient in which the implantable device is inserted is not encumbered by the mobility of the external device.

At block 718, the parameter readings are received at the external device external to the body. At block 720, the parameter readings are processed by the external device, for example, for storage and/or display.

At block 722, the implantable device is removed from the body, for example, via a catheter like device (not shown). At block 724, bodily parameters stored within the implantable device at block 708 are, optionally, compared to readings within the external device that were received by the external device from the implantable device while the implantable device was still within the body. This allows comparison of transmitted data with data stored in the implantable device and provides confirmation that information received via transmission reflects the actual readings of the implantable device. Thus, potential corruption of the transmitted signal due to transmission through biological tissues of the body can be identified and accounted for in future transmissions. It is contemplated that the transmitted signals may be encoded in a manner that minimizes the potential for corruption due to transmission through biological tissues, thereby making the step within block 724 unnecessary.

Figure 8:
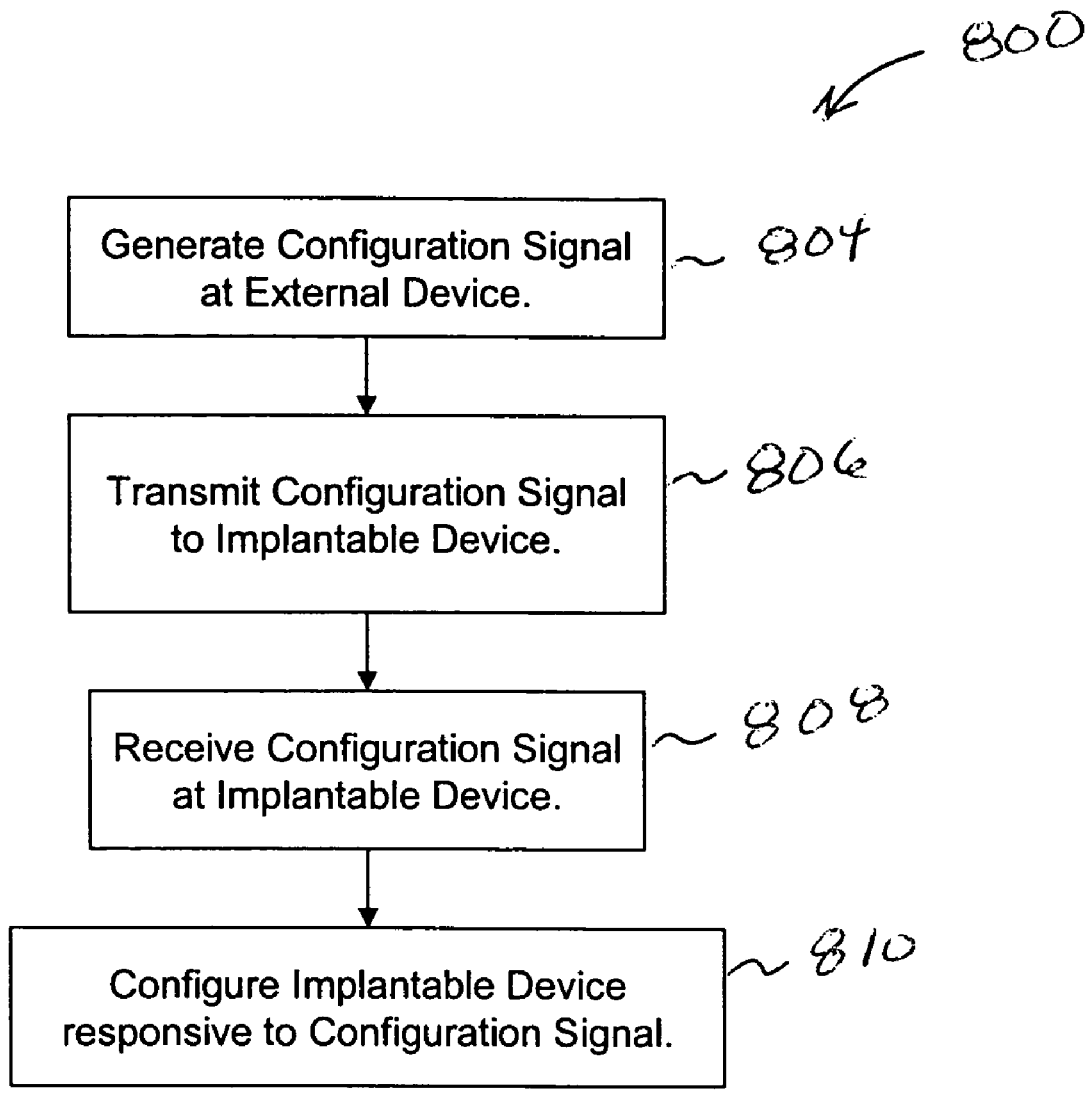
FIG. 8 is a flow chart of alternative exemplary steps performed by the exemplary telemetric monitoring system of FIG. 1 in accordance with the present invention.

FIG. 8 depicts a flow chart 800 of other exemplary steps performed by a telemetric monitoring system 100 (FIG. 1). Processing begins at 802 with the generation of a configuration signal by a external device 104 at block 804. In an exemplary embodiment the configuration signal is a signal for configuring an implantable device 106. For example, the configuration signal may be a signal that configures the implantable device such that it is on or off. Other potential configuration signals may configure the internal device to turn on at certain times, for example, two hours every twelve hour period, fifteen minutes every hour, etc. Other such configuration will be understood by those of skill in the art. Periodically turning the implantable device off conserves power, thereby extending the useful life of the implantable device.

At block 806, the external device transmits the configuration signal to the implantable device.

At block 808, the implantable device receives the configuration signal. At block 810, the implantable device is configured responsive to the received configuration signal, for example, by the processor within the implantable device.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A telemetric monitoring method for monitoring parameters within a body of an animal, the method comprising:
   inserting an implantable device into a urinary bladder within the body;
   sensing and storing one or more bodily parameters within a body, wherein the bodily parameters include pressure within a urinary bladder and the steps of sensing and storing are performed by the implantable device;
   generating a parameter transfer signal external to the body;
   receiving the parameter transfer signal within the body;
   responsive to receipt of the parameter transfer signals transmitting the bodily parameters from within the body for receipt by a device external to the body;
   receiving the bodily parameters transmitted from within the body at the device external to the body;
   removing the implantable device from the urinary bladder; and
   comparing the parameter readings stored in the implantable device to the transmitted stored parameter readings received external to the body.

2. The method of claim 1, wherein the step of generating the parameter transfer signal comprises the steps of:
   receiving a transfer request signal;
   generating the parameter transfer signal responsive to the transfer request signal; and
   transmitting the generated parameter transfer signal.

3. The method of claim 1, wherein the sensing and storing step comprises the step of:
   storing bodily parameters within the body responsive to a storage parameters signal generated external to the body.

4. A telemetric monitoring method for monitoring bodily parameters within a body of an animal; the method comprising the steps of:
   inserting an implantable device into a urinary bladder within the body;
   sensing a bodily parameter, wherein the bodily parameter is pressure within the urinary bladder;
   storing the sensed bodily parameter readings within the body, wherein the steps of sensing and storing are performed by the implantable device;
   receiving a parameter transfer signal within the body from a source external to the body;
   transmitting the stored sensed bodily parameter readings from within the body for receipt external to the body responsive to the received parameter transfer signal;
   removing the implantable device from the urinary bladder; and
   comparing the parameter readings stored in the implantable device to the stored parameter readings transmitted for receipt external to the body.

5. The method of claim 4, wherein the storing step comprises the step of:
   storing bodily parameters within the body responsive to a storage parameters signal generated external to the body.

* * * * *